Figure 1:
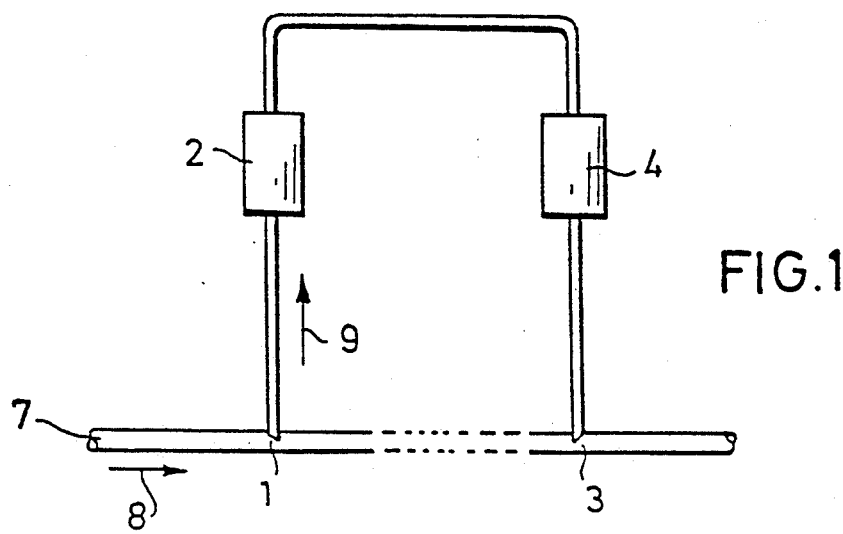

United States Patent [19]

Schmoll et al.

[11] Patent Number: 5,209,717

[45] Date of Patent: May 11, 1993

[54] METHOD AND DEVICE FOR LOCAL APPLICATION AND REMOVAL OF ACTIVE SUBSTANCES AGAINST SOLID TUMORS

[75] Inventors: Hans-Joachim Schmoll; Ekkehard Schmoll, both of Hannover; Edmund R. Lax, Essen, all of Fed. Rep. of Germany

[73] Assignee: Pharma Biotechnologie Hannover GmbH, Hannover, Fed. Rep. of Germany

[21] Appl. No.: 224,319

[22] Filed: Jul. 26, 1988

[30] Foreign Application Priority Data

Feb. 21, 1987 [DE] Fed. Rep. of Germany ....... 3705637

[51] Int. Cl.$^5$ ............................................. A61M 37/00
[52] U.S. Cl. .......................................... 604/5; 604/4; 604/49; 604/52
[58] Field of Search ........................... 604/406, 49, 52

[56] References Cited

U.S. PATENT DOCUMENTS

| | | | |
|---|---|---|---|
| 4,337,760 | 7/1982 | Rubin | 604/52 |
| 4,605,394 | 8/1986 | Skurkovich | 604/5 |
| 4,610,662 | 9/1986 | Weikl et al. | 604/53 |
| 4,867,742 | 9/1989 | Calderon | 604/101 |

FOREIGN PATENT DOCUMENTS 3535641 4/1987 Fed. Rep. of Germany.

OTHER PUBLICATIONS

Howell, Seminars in Oncology, vol. XII, No. 3, Suppl. Sep. 4, 1985; pp. 17-22.
Clark, et al., J. Neurosurg. 62, 576-579 (1985).
Oldfield, et al., J. Neurosurg. 63, 726-732 (1985).
Oldfield, et al., Cancer Res. 47, 1962-1967 (1987).
Rote Liste, Zytostatica and Blocker of Methastases.
Bersani, Laura et al., "Involvement of Tumour Necrosis Factor in Monocyte-Mediated Rapid Killing of Actinomycin D-Pretreated WEHI 164 Sarcoma Cells", Immunology, vol. 59, pp. 323-326, 1986.
Aggarwal, Bharat B., et al., "Characterization of Receptors for Human Tumour Necrosis Factor and Their Regulation by $\tau$-Interferon", Nature, vol. 318, Dec. 19-26, 1985.
Balkwill, Frances R., et al., "Human Tumor Xenografts Treated with Recombinant Human Tumor Necrosis Factor Alone or In Combination with Interferons", Cancer Research, vol. 46, pp. 3990-3993, Aug. 1986.
Fransen, Lucie, et al., "Recombinant Tumor Necrosis Factor: Its Effect and Its Synergism with Interferon-$\tau$ on a Variety of Normal and Transformed Human Cell Lines", Eur. J. Cancer Clin. Oncol., vol. 22, pp. 419-426, 1986.

Primary Examiner—Stephen C. Pellegrino
Assistant Examiner—Michael Rafa
Attorney, Agent, or Firm—Wegner, Cantor, Mueller & Player

[57] ABSTRACT

Described are a method and a device for the application and the removal of locally applied active substances against solid tumors, which device consists of a catheter (1) to be positioned distally to the tumor for the collection of blood coming from the tumor, a pump (2) and a catheter (3) connected thereto and returning the blood into the body. The device is characterized in that between the two catheters (1, 3) there is present at least one container (4) capable of allowing blood to pass therethrough and containing immobilized substances having high affinity against the applied active substance.

12 Claims, 5 Drawing Sheets

METHOD AND DEVICE FOR LOCAL APPLICATION AND REMOVAL OF ACTIVE SUBSTANCES AGAINST SOLID TUMORS

The present invention relates to a method and a device for the application and removal of active substances against solid tumors, which are locally applied. The device consists of a catheter to be positioned distally to the tumor for the collection of blood coming from the tumor, a pump and a catheter connected thereto and returning the blood into the body. In the method the active substances against solid tumors are applied locally.

In the most cases, chemotherapy of cancer suffers from a severe drawback: antitumor agents cannot be applied in such dosage as required, because the side effects of the applied drug are too severe. The problems of modern chemotherapy of cancer are explained taking the "Biological Response Modifiers" (BRM) as an example. Recently, said class of substances has been introduced in cancer-therapy.

In vitro investigations with cell cultures of human and animal cells and in vivo studies with species-specific tumors transplanted into animals and human tumors have shown that many Biological Response Modifiers (BRM's) may exert an antineoplastic effect. The term "Biological Response Modifiers" comprises a group of proteins and glycoproteins which are released from a cell and exert an influence on other cells or on the BRM-synthesizing cell itself, said influence becoming manifest by changes in metabolism or other functions of the cell. Within a narrower meaning, the term is intended to designate the secerned active substances of blood cells and blood cell precursors—e.g. interferons, interleukins, colony stimulating factors, tumour necrosis factor, lymphotoxins, transforming growth factors and/or further stimulating or inhibiting factors—and all other factors which today are connected with the terms lymphokine, monokine and cytokine. As far as known, the antineoplastic activity in vivo, on the one hand, is due to a systemic stimulation of the own immune defense, while, on the other hand, in vitro experiments and xenograft studies suggest that a direct cytotoxic destruction of the tumor cells themselves or their associated blood vessels occurs. Thus, a local reaction takes place. In many of the antitumor agents, e.g. BRM's the range between the effective dose and the toxic dose (therapeutic window) for man is either very small or does not even exist at all, namely if the toxic effects prevail. Thus, for example, patients treated with Interleukin-2 (IL-2) must be cared for in an intensive care unit.

Okuno et al., Cancer 58 (1986), pp. 1001–1006, describe a method wherein patients suffering from liver carcinoma (hepatoma) had been administered by means of an arterial infusion with autologous spleen cells which had been previously activated in vitro with IL-2. In a similar way another Japanese group attempted to treat liver cancer with lymphocytes injected into arteria leading to the liver, wherein the injected lymphocytes were to be activated by simultaneous continous infusion of small amounts of IL-2 (see Biotechnology in Japan, Newsservice, Vol. 5, No. 3, December 1986).

The new method of the regional application of toxic active substances offers a possibility to medicine to mitigate these problems by that the regionally applied dose is much in excess of the threshold value of systemic toxicity.

The method for the treatment of solid tumors with antitumor agents, e.g. BRM's according to the present invention is characterized in that BRM's at a high dose are administered in an afferent vessel in the vicinity of the tumor and in an efferent vessel are passed to the blood circulation system and diluted there. Thereby, the dose of the active substance to be employed can be enormously increased. The method is suitable for the treatment of solid tumors, more specifically of tumors of the lower abdomen, the liver and the extremities. The improved metered addition by means of the method according to the invention is to be exemplified by a liver tumor. The liver amounts to about 3% of the total body mass. Thus, using regional perfusion about 35 times the dose of the involved active substance can be employed.

The method also allows a combined and/or sequential application of the antitumor agents, e.g. BRM with 1. chemotherapeutics;
2. a second BRM;
3. a monoclonal antibody;
4. cytotoxics bonded to monoclonal antibodies;
5. factors sensitizing the tumor or tumor tissue.

A sensibilization of the tumor cells, for example, is effected by the gamma-interferon which is supposed to increase the number of receptors for the BRM's (e.g. TNF) (Aggarwal et al., Nature 318, 665–667, 1985, "Characterization of receptors for human tumour necrosis factor and their regulation by gamma-interferon"; Balkwill et al., Cancer Res. 46, 3990–3993, 1986, "Human tumour xenografts treated with recombinant human tumor necrosis factor alone or in combination with interferons; Fransen et al., Eur. J. Cancer Clin. Oncol. 22, 419–426, 1986, "Recombinant tumor necrosis factor: its effect and its synergism with interferon-gamma on a variety of normal and transformed human cell lines"). Actinomycin D is also capable of sensitizing tumor cells (Bersani et al., Immunology 59, 323–325, 1986, "Involvement of tumour necrosis factor in monocyte-mediated rapid killing of actinomycin D-pretreated WEHI 164 sarcoma cells; Creasy et al., Biological Therapy of Cancer: A 1986 Update, Chapel Hill 1986, "Studies on the cytotoxicity of tumor necrosis factor in vitro").

A large part of the antitumor agent is adsorbed by the tumor or tumor-containing organ. However, the remainder must be diluted in the systemic circulation to such an extent that toxic phenomena do not occur. However, if it is desired to administer the active substance at such a dosage which causes toxic phenomena to occur even under the dilution conditions as described above, then the toxic effects can be evaded only by removing the excess of the active substance. For the removal of the antitumor agent it is not recommendable to employ the conventional methods of blood filtration, when the antitumor agents are relative large polar molecules like BRM's. For example, in the case of intoxications the blood is passed over an active charcoal filter. Said filters have the drawback of that they are non-specific. In addition, they are out of consideration for the filtration of biopolymers, more specifically of peptides and proteins from blood already for the reason that the range of application of the activated carbon filters is limited to relatively small non-polar compounds. On the other hand, the membranes as conventionally used in the dialysis/hemofiltration have only small pore sizes so that the larger antitumor agents like BRM's will not permeate into the dialyzate and, thus, cannot be removed.

If the pores of the dialysis membrane will be enlarged, then, in addition to the active substances (BRM's) also proteins enter the dialyzate, the removal of which is not desired. The non-specifity of a membrane having sufficiently large pores for separating, for example, administered BRM would result in unnecessarily endangering the patient by stressing the patient's metabolism.

In the unexamined German patent application P 35 23 616 there is disclosed a filter for separation of pathogenic viruses, bacteria, moulds and metabolic products from blood. This filter consists of a physiologically compatible polymer, which surface was coated with homologous or monoclonal immunoglobulins against the respective substances. The separation of the pathogenic substances from blood occurs by pumping the blood from the body through the filter by means of a blood-pump. The whole blood volume is lead through the filter in a similar manner as in the method of hemodialysis. The substances to be removed are binding to the antibodies and are filtered out of the blood streaming through the filter.

It is one object of the invention to provide a method for the application of active substances against solid tumors avoiding the above mentioned drawbacks.

Another object of the present invention is to provide a device which enables the removal from the blood to be effected of substances active against tumors so that the active substances can be employed at an otherwise toxic dosage. Such a device is intended also to enable the specific removal of the active anti-tumor substance. A further requirement is that the device allows a combined and/or sequential application of 1. chemotherapeutics and BRM;
2. two different BRM's;
3. BRM and monoclonal antibodies;
4. BRM and cytotoxics bonded to monoclonal antibodies; and
5. factors sensitizing the tumor or tumor tissue together with BRM.

In the method of the invention the active substance against the solid tumor is applied locally.

The device of the invention for the removal of active substances locally applied against solid tumors comprises a catheter (1) to be positioned distally to the tumor for the collection of blood coming from the tumor, a pump (2) and a catheter (3) connected thereto and returning the blood into the body. The device further comprises between the two catheters (1, 3) at least one container (4) capable of allowing blood to pass therethrough which contains immobilized substances having high affinity against the applied active substance.

A preferred embodiment of the device according to the invention is the embodiment comprising the two catheters (1) and (3) as a double-bore catheter wherein the efferent leg of the catheter (1) is shorter than the afferent leg of the catheter (3). Double catheters are well known as so-called Aigner catheters in clinical practice. Aigner catheters are disclosed in the German patent DE-PS 32 14 397. Another embodiment of the device according to the invention consists of that at least one elastic balloon (cuff) (6a) is present distally to the opening of the catheter (1) for blood collection which serves as a shut-off means of the blood vessel. This embodiment has the advantage over the open arrangement of that excess active substance cannot escape into the direction of the venous blood flow due to diffusion or venous blood flow and all of the blood being accumulated distally to the tumor has to pass through the container (4). It is also possible to locate a second elastic balloon (cuff) (6b) upstream before the blood vessels exiting from the tumor in order to completely close-off the blood vessel. In this embodiment the collection opening of the catheter (1) is between the two cuffs (6a) and (6b). The cuffs (6a, 6b) can be expanded by a gaseous or liquid medium, e.g. physiological saline.

Figure 5:
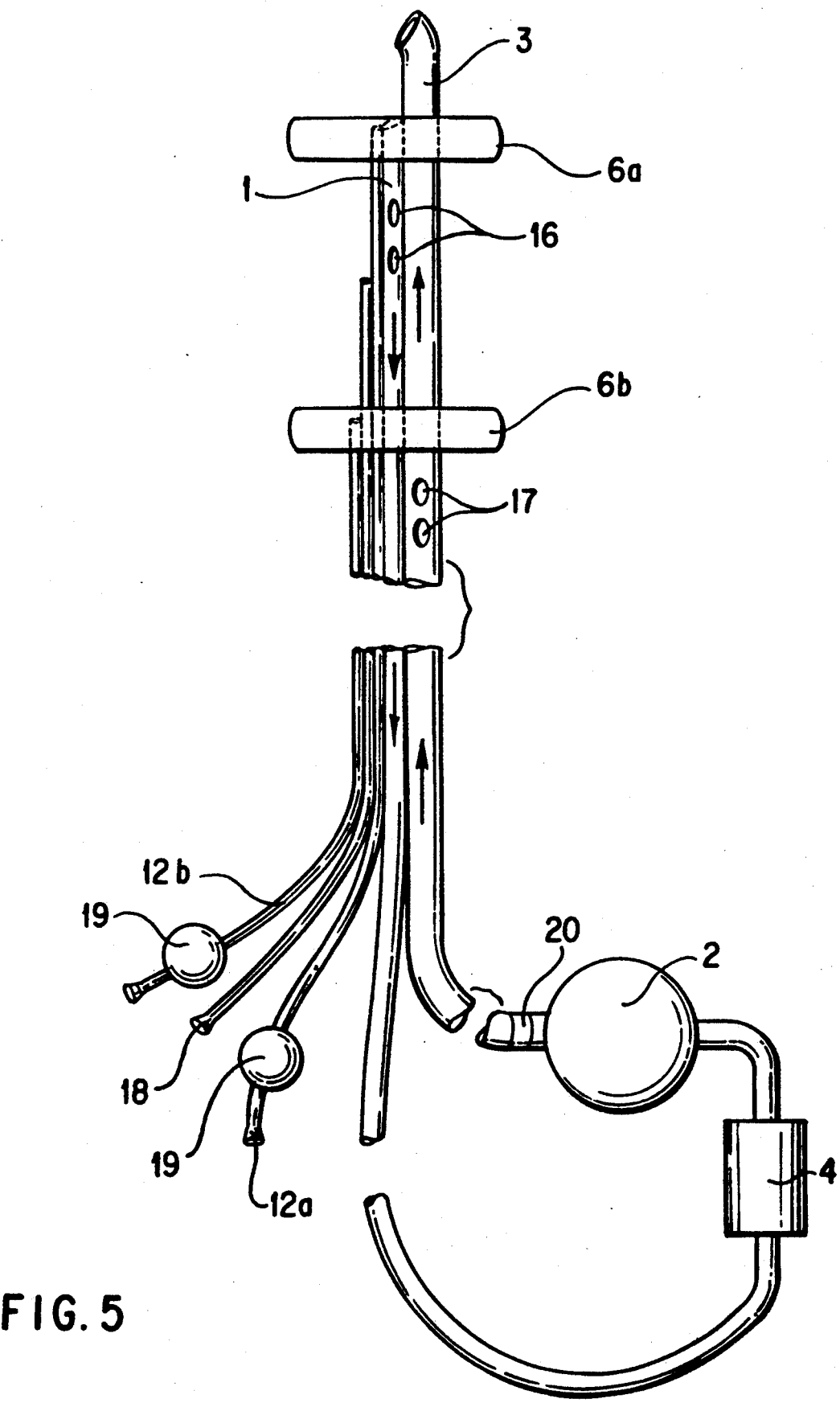

A preferred embodiment of the present invention is verified by the device shown in FIG. 5. This particular form of a double-bore catheter is introduced into the *Vena cava* via the *Vena femoralis*. The double-bore catheter is placed in such a way that the upper cuff (6a) lies above the diaphragm and the other cuff (6b) is situated shortly behind the point where the *Vena cava* enters the liver. Alternatively, the blood is led back into the circulation via the *Vena subclavia*. In the latter embodiment it becomes possible to modify the size of the catheter. The exact position of the catheter is controlled by suitable processes like, for example, angiography.

In the container (4) of the device according to the invention there are immobilized substances against active substances, more particularly those from blood cells and/or blood cell precursors. In a preferred embodiment of the invention the immobilized substances are such as antibodies. Also usable in the device according to the invention are antibodies directed against substances from the class comprising lymphokines, monokines and/or cytokines, more specifically interferons, interleukins, colony stimulating factors, tumour necrosis factor, lymphotoxin, transforming growth factors and/or further stimulating or inhibiting factors.

The device according to the invention permits to meet the requirement as set therefor, namely, to be suitable not only for the administration of mono-preparations of the antitumor agents, but also for aimed combination therapies, more particularly 1. a combination of chemotherapeutics and BRM; such therapies are clinically more efficient than the sole administration of mono-preparations. The BRM is neutralized by monoclonal antibodies and removed. The chemotherapeutic may be removed—if desired—by means of activated carbon, hemofiltration or monoclonal antibodies as well.
2. a combination of two different BRM's; both of the BRM's are neutralized and removed by monoclonal antibodies.
3. a combination of BRM and monoclonal antibodies (MAB's).
4. a combination of BRM and MAB-bound cytotoxic compounds (targeted chemotherapy). BRM as well MAB-derivaties can be removed by the appropriate MAB's.
5. a sensibilization of the tumor tissue; due to the presence of the arterial permanent catheters it is possible to perfuse the tumor several times and with different agents. This fact is utilized for increasing the sensitivity of the tumor tissue by means of pre-treatment. This pre-treatment consists of a perfusion with compounds which sensitize the cells to the BRM's or the combination therapeutics. The sensibilization may be effected by an increase in the number of the BRM receptors, the de novo induction of receptors previously not present, alterations in the intracellular BRM metabolism or other cellular events.

The active substance which may be administered by means of the device according to the invention is understood to include substances capable of sensitizing the tumor or tumor tissue. It is to be understood that also lymphokine activated killer cells can be applied with the device of the invention.

Another advantage of the device of the invention is that it allows the method of regional perfusion of the liver avoiding severe operations and their complications.

FIG. 1 shows a highly schematic graphic representation of the device according to the invention. In a vein (7) exiting from a tumor or tumor tissue, at a location distally to the tumor there has been inserted the opening of the venous catheter (1). The blood flow direction is indicated by the arrow (8). By means of the pump (2) the blood is drawn into the direction of the arrow (9) through the opening of the venous catheter (1), forced through the container (4) containing immobilized antibodies against the applied active substance and returned to the blood circulation system at the inlet of the venous catheter (3) inserted in the same or a different blood vessel. In the course thereof the antibodies present in the container (4) will bind the excess of the applied active substance and remove same from the blood circulation.

Figure 2:
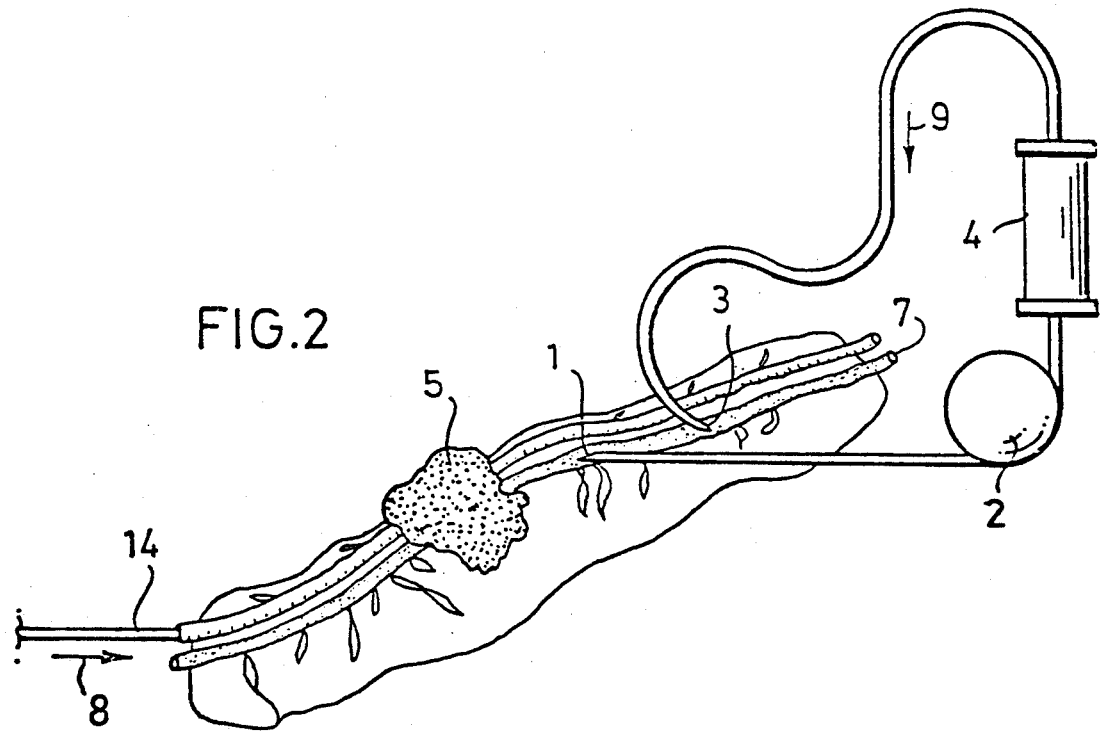

FIG. 2 schematically shows an embodiment of the device according to the present invention by means of which embodiment a local application against solid tumors of the active substance can be carried out through an arterial catheter (14). In a vein (7) exiting from an intestinal tumor (5) at the side distally to the tumor (5) there has been inserted the opening of the venous catheter (1). The blood flow direction is indicated by the arrow (8). By means of the pump (2) the blood is aspired in the direction of the arrow (9) through the opening of the venous catheter (1), forced through the container (4) containing immobilized antibodies against the applied active substance and returned to the blood circulation system at the inlet of the venous catheter (3) inserted in the vein (7) at a different location. In the course thereof the antibodies present in the container (4) will bind the excess of the applied active substance and remove same from the blood circulation. Through the arterial catheter there may also be applied the substances sensitizing the tumor.

Figure 3:
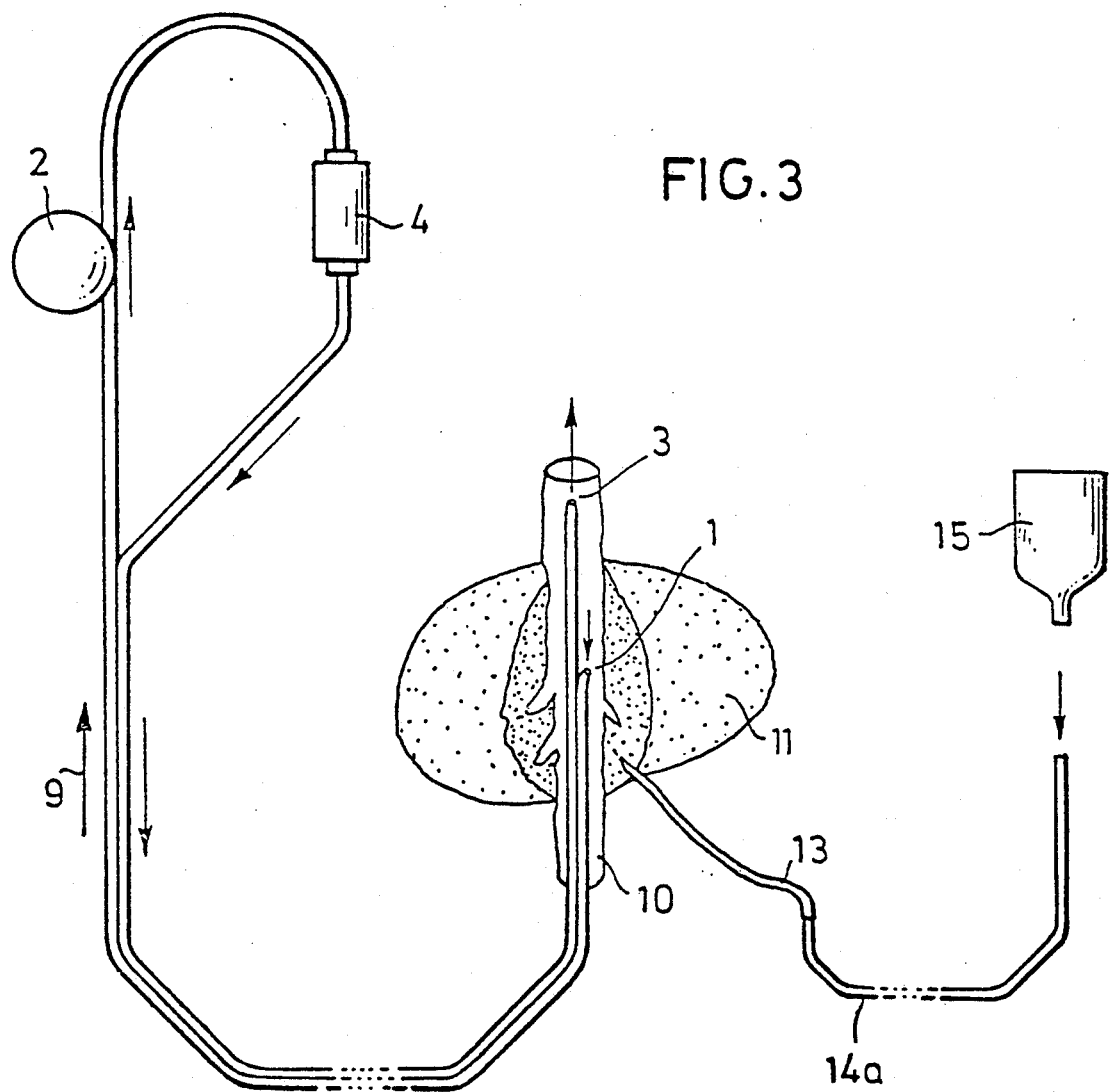

FIG. 3 schematically shows the embodiment in the form of a double catheter of the device according to the present invention, which double catheter has been inserted in the *Vena cava* (10) for the treatment of a liver tumor (11). By means of an arterial catheter (14a) the active substance (for example BRM) from the supply vessel (15) is locally applied through the *Arteria hepatica* (13) in the vicinity of the tumor or tumor tissue. The excessive active substance discharged into the blood stream from the tumor (for example BRM) is removed together with the blood through the opening of the venous catheter (1) by means of the pump (2), forced through the container (4) containing the immobilized antibodies against the applied active substance and returned to the blood circulation system via the opening of the venous catheter (3). In a modification of the embodiment of FIG. 3 a second active substance can be applied through the catheter (3).

Figure 4:
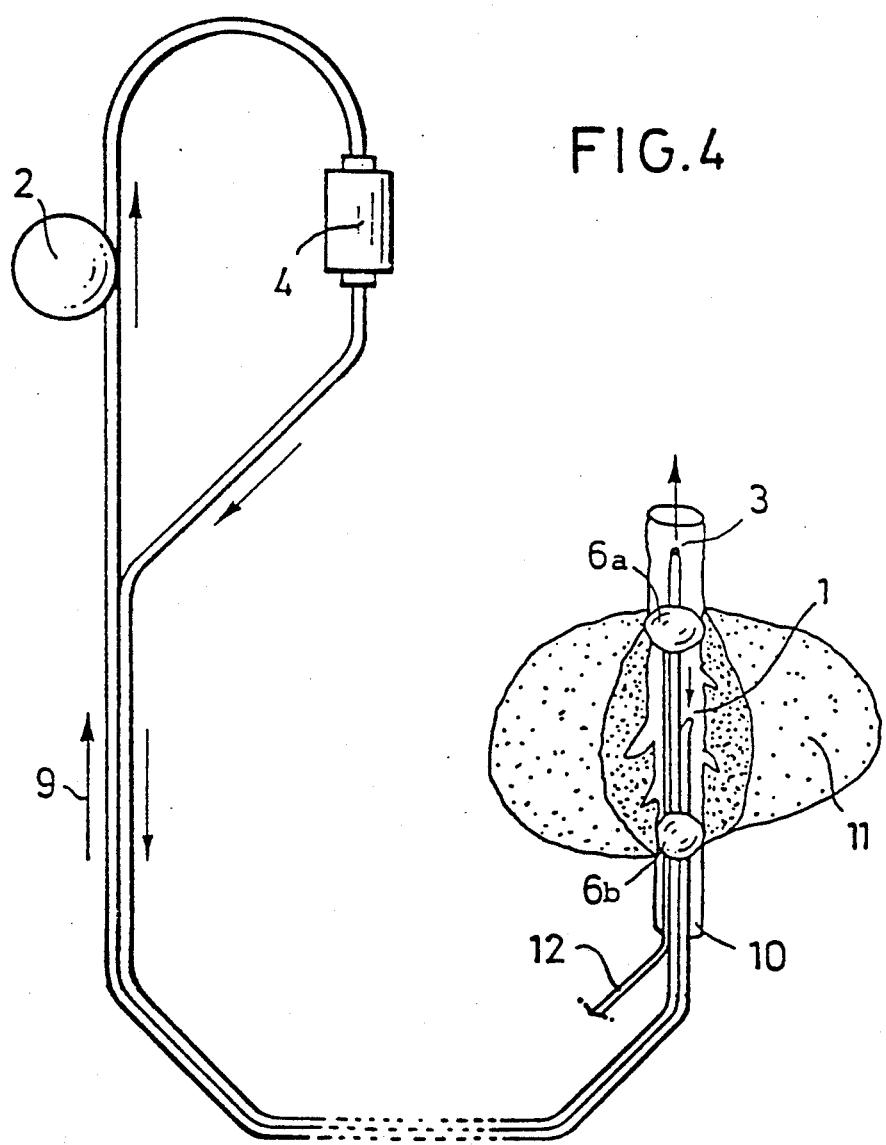

FIG. 4 schematically shows the embodiment in the form of a double catheter of the device according to the present invention, which double catheter has been inserted in the *Vena cava* (10) for the treatment of a liver tumor (11). Between the balloons (cuffs) (6) expandable by a gas or a fluid through the line (12) there is positioned the opening of the catheter (1) for collecting the blood, which is returned into the blood stream through the opening (3) of the double catheter on the other side of the cuff (6) in the upstream position, after the collected blood by means of the pump (2) has been forced through the container (4) containing the antibody. Preferably, the cuffs are expanded by filling in physiological saline.

FIG. 5 shows another device of the invention, which is particularly suitable for the treatment of liver tumors. The double catheter of the invention is formed advantageously as a double-bore catheter having a smaller inner diameter in the efferent leg (1) than in the afferent leg (3). The afferent leg (3) is longer than the efferent leg (1) and has an inner diameter of from 0.3 to 1.2 cm, more preferably of 0.7 cm, whereas the inner diameter of the efferent leg (1) is from 0.2 to 0.7 cm, more preferably 0.3 cm. The cuffs (6a) and (6b) are arranged in a distance of each other of from 8 to 10 cm, more preferably 9 cm, and in such a way that the orifice of the efferent leg (1) of the catheter is situated before the cuffs. The efferent leg (1) of the double-bore catheter shows a few oval openings (16), more preferably two openings (16) between the two cuffs (6a) and (6b). The afferent leg (3) of the catheter also shows at least two openings (17) which are arranged in line before the lower cuff (6b). The afferent leg (3) protrudes the cuff (6a) placed towards the tip of the catheter between 1 and 2 cm, more preferably 1.5 cm.

The lines (12a) and (12b) for expanding the cuffs (6a) and (6b) can also be replaced by one line, which either branches into two arms providing the elastic cuffs or which line has an opening in the cuff (6b). The inner diameter of the line(s) (12) is from 0.05 to 0.2 cm, preferably 0.08 cm. Preferably, the cuffs are expanded by filling in physiological saline.

The line (18) leads into the space which is defined by the cuffs (6a) and (6b). The line (18) is used for supplying contrast medium into the space between the cuffs (6a) and (6b).

At the end of the lines (12a) and (12b), two elastic balloons (19) are arranged in the external area of the patient's body. These balloons (19) serve as a control for the filling of the cuffs. Preferably, the balloons (19) as well as the cuffs are made from silicon rubber or material consisting essentially of polyvinylchloride. The wall thickness of the device is of from 0.05 to 0.2 cm, more preferably 0.1 cm. Only in the area of the cuffs the wall thickness is of from 0.1 to 0.3 cm, more preferably 0.2 cm.

Optionally there might be provided an outlet (20) for taking off blood and/or giving heparin. It is also possible to use the device without the container (4) containing immobilized substances with high affinity against the applied active substance. The active substance can be removed by other means, e.g. hemofiltration.

Figure 6:
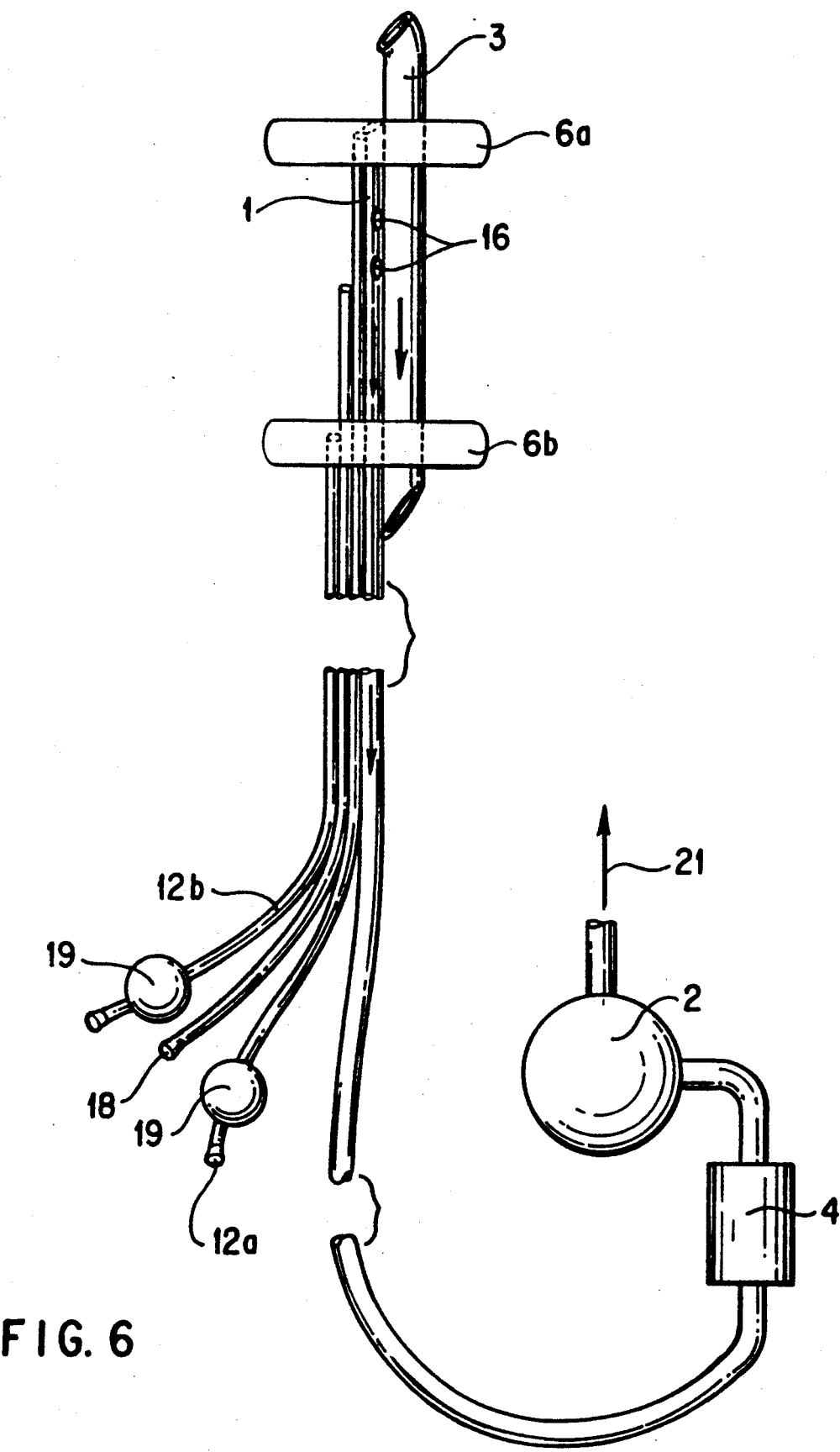

FIG. 6 shows another preferred embodiment of the invention. The difference of that particular device and that of FIG. 5 is the different refill of blood. The filtered blood is led back into the circulation via the *Vena subclavia* in direction of the arrow (21) and not via the *Vena cava*. This particularly preferred embodiment comprises an afferent leg (3) which one end is located upstream in a certain distance of cuff (6b) so that it shunts the space defined by the cuffs (6a,b). This is particularly advantageous because it becomes possible to use larger tubes when the blood is led back via the *Vena subclavia*. Therefore, the whole method is better controllable and the double-bore catheter can be of more suitable size.

The device according to the invention is suitable for use in a perfusion method for the treatment of solid tumors by local application of substances which are active against the tumors, in which method the blood is collected at a location distally to the tumor by means of a catheter, is pumped through a container containing carrier-bound antibody against the active substance and returned into the body. A particular embodiment of the method utilizes the shut-off effect provided by the elastic cuffs (6a) and (6b) positioned distally to the opening of the catheter (1) for collecting the blood. This embodiment is particularly advantageous since it prevents the toxic active substance from being uncontrollably distributed in the body due to diffusion or venous blood flow. The shut-off barrier also ensures that all of the blood being accumulated distally to the tumor passes through the container (4).

The device according to the invention also allows a perfusion method to be carried out in the course of which the tumor or tumor tissue is sensitized by the application of active substances.

In the method of the invention the treatment of solid tumors is effected by local application of active substances against the tumor. As substances can serve all anti-tumor agents, for example such as Biological Response Modifiers (BRM) as defined above. The active substances have to be removed or their effects have to be neutralized in order to avoid possible side-effects. According to the invention, this is achieved by removing the active substance with the container (4) of the device of the invention containing immobilized substances having high affinity against the active substances. However, the effects of the locally applied therapeutically active substances against the solid tumors also can be neutralized by infusing a first active substance against the solid tumor into an afferent blood vessel of the attacked organ and a second active substance, which is capable to inactivate the effect of the first active substance (a) either by direct interaction of the second substance with the first substance after infusion distally to the tumor-containing organ or (b) by indirect interaction infusing distally to the tumor-containing organ and (c) both active substances are filtered out of the patient's blood, whereby the blood is withdrawn distally to the tumor, pumped through a container containing substances, which are capable to bind the applied active substances and returning the blood into the patient's body.

The direct interaction is, for example, caused by a chemical reaction of the first and the second active substance. For example, after application of the active substance against the solid tumor, there is applied an enzyme which converts the active substance in an inactive substance, which does not have severe side-effects. The direct interaction of both substances can be based on either covalent or ionic interaction. The direct interaction can also be based on antigen-antibody interaction. In this case, the active substance is inactivated by blockage of the active sides, which cause, i.a., the side-effects.

Indirect interaction of both substances is to be understood as the inactivation of the effect of the first active substance based on indirect interaction of the first and the second active substance, effecting a blockage of the receptors of the first active substance by the secondly applied active substance. When a substance with antagonistic effects of the active substance is applied in sufficient concentration, the receptors of the active substance will be blocked and the active substance cannot develop its severe side-effects. The inactivation of the effect of the active substance can also be achieved by application of a second substance, which neutralizes the effects of the first active substance by interaction with different receptors causing a response, which is in a physiological sense contrary to the physiological response caused by the first active substance.

Optionally, a filter placed in the external area of the patient's body provides the removal of both substances either bound in complex form or individually, when they do not interact forming a complex.

As the active substances sensitizing the tumor or tumor tissue, there are particularly considered lymphokines. It is further made possible to apply a method wherein BRM as an active substance is combined with 1. chemotherapeutics;
2. a second BRM;
3. a monoclonal antibody; and
4. a cytotoxic compound bonded to a monoclonal antibody.

A procedure adopted for permanent perfusion is also ensured by using the device according to the invention. This method can be used with all organs, tumors and parts of the body suitable for application of a perfusion, for example abdominal tumors, liver tumors, tumors of the extremities etc.

The use of immobilized antibodies against active substances for the treatment of tumors serves to remove the excess of active substance which otherwise would cause toxic phenomena to occur in the patient.

The antibodies directed against the active substances to be applied may be immobilized on any suitable carrier. One carrier suitable for the antibodies to be bound, for example, is activated agarose, and particularly Sepharose ®. This matrix, for example, is encapsulated in cellulose bodies having a suitable pore size, filled into the container (4) and sterilized (e.g. by means of gamma rays). Then under sterile conditions the antibody is introduced into the container (4) so that a conjugation between the antibody and the matrix takes place. The excess of antibody may be removed from the container with a sterile saline solution.

The invention is further illustrated by way of the following Example.

EXAMPLE

Tumor Necrosis Factor (TNF), a physiological protein having a molecular weight of 17,000 is a synthesis product of macrophages. TNF serves to entirely separate functions in tumor-bearing mammals.

On the one hand, TNF has a direct cytotoxic effect on the tumor cells, while, on the other hand, TNF causes the reserve forces of the body to be released, which when chronic leads to serious emaciation (cachexia) of the patient and all other symptoms of an endotoxic shock. The two responses to TNF doses, the anti-tumor effect, on the one hand, and the cachectic effect, on the other hand, are by no means represented to the same extents in different species. Thus, while mouse appears to be relatively resistant to cachexia, however; reacts sensitively to the anti-tumor properties of TNF, with man the situation is inverse. Namely, the systemic administration of TNF rather leads to cachexia and endotoxic shock than to a remission in tumor patients, however, by injection of TNF into the tumor tissue there might be induced a haemorrhagic nekrosis.

In the regional perfusion of the liver there can be locally achieved an about 35-fold increase of the systemic dose, since the liver only amounts to about 3,5% of the total body mass. However, by using the device according to the invention, more specifically in the form of the double bore catheter in the *Vena cava* via the *Vena femoralis*, and passing the blood over a suitable filter having a sufficient capacity, factually the excessive active substance is removed to a far extent. Thus it is also possible, accordingly to increase the dose of the active substance to be applied. TNF is introduced via the *Arteria heoatica* into the liver by means of a permanent catheter. In a corresponding efferent vessel, the *Vena cava*, there is inserted a double bore catheter or, in the case of the *Vena subclavia*, a single bore catheter. By means of these catheters the blood is withdrawn and urged through an anti-TNF filter consisting of matrix-bound anti-TNF-monoclonal antibodies.

We claim:

1. A method for the treatment of solid tumors, wherein a therapeutically effective amount of active substances against the solid tumors are locally injected, characterized in that (a) the active substance is infused into an afferent blood vessel of a tumor-containing organ, (b) a second active substance, which is capable to inactivate the effect of the first active substance, is infused distally to the tumor-containing organ, and (c) both active substances are filtered out of the patient's blood, wherein the blood is withdrawn distally to the tumor, pumped through a container containing substances, which are capable to bind the active substances, and returning the blood into the patient's body.

2. The method according to claim 1, characterized in that the second active substance inactivates the effect of the first active substance by direct interaction caused by chemical reaction of the first and the second active substance.

3. The method according to claim 2, characterized in that the chemical reaction is a covalent or an ionic interaction.

4. The method according to claim 1, characterized in that the second active substance inactivates the effect of the first active substance by direct non-covalent interaction of the first and the second applied active substance based on antigen-antibody interaction.

5. The method according to claim 1, wherein the second active substance is an antagonist of the first active substance, which blocks the receptors of the first active substance and inactivates the effect of the first active substance.

6. The method according to claim 1, wherein the second active substance reacts with receptors on the first active substance to cause a physiological response contrary to the physiological response caused by the first active substance, which inactivates the effects of the first active substance.

7. The method according to claim 1, characterized in that the active substance belongs to the group comprising the Biological Response Modifiers (BRM's).

8. The method according to claim 1, characterized in that the active substance is injected in a vessel afferent to the tumor.

9. The method according to claim 1, characterized in that the blood is withdrawn through a catheter distally to the tumor, is pumped through a container containing carrier-bound substances having high affinity against the active substance and then is returned into the body.

10. The method according to claim 9, characterized in that distally to the opening of the catheter (1) for collecting blood there is present at least one elastic cuff (6a) for shutting-off the blood vessel.

11. The method according to claim 1, characterized in that lymphokines are employed as active substances for sensitizing the tumor tissue.

12. The method according to claim 1, characterized in that there are employed in combination chemotherapeutics with Biological Response Modifiers (BRM's), two different BRM's, monoclonal antibodies with BRM's and BRM's with cytotoxic compounds bound to monoclonal antibodies.

* * * * *